US00PP24890P2

(12) United States Plant Patent
Allen

(10) Patent No.: US PP24,890 P2
(45) Date of Patent: Sep. 16, 2014

(54) ***LEUCANTHEMUM* PLANT NAMED 'SHAPCOTT SUMMER CLOUDS'**

(50) Latin Name: *Leucanthemum×superbum*
Varietal Denomination: Shapcott Summer Clouds

(71) Applicant: Anita Allen, South Molton (GB)

(72) Inventor: Anita Allen, South Molton (GB)

( * ) Notice: Subject to any disclaimer, the term of this patent is extended or adjusted under 35 U.S.C. 154(b) by 87 days.

(21) Appl. No.: 13/815,089

(22) Filed: Jan. 30, 2013

(51) Int. Cl.
*A01H 5/00* (2006.01)

(52) U.S. Cl.
USPC ..... Plt./285

(58) Field of Classification Search
CPC ..... A01H 5/00
USPC ..... Plt./285
See application file for complete search history.

*Primary Examiner* — Anne Grunberg
(74) *Attorney, Agent, or Firm* — Penny J. Aguirre

(57) ABSTRACT

A new cultivar of *Leucanthemum*, 'Shapcott Summer Clouds', characterized by its capitulums with numerous fine ray florets (1 mm in width) that are arranged in a regular pattern nearly horizontal from the disk portion, its cold hardiness to −20° C., its flower stems that stand erect and do not lodge, its height of 45 to 61 cm, its dependably long-lived habit, its use as a long lived cut flower, and its deep green healthy foliage that has been observed to be disease free under the conditions tested.

2 Drawing Sheets

Botanical classification: *Leucanthemum×superbum.*
Variety denomination: 'Shapcott Summer Clouds'.

CROSS REFERENCE TO RELATED APPLICATIONS

This application is co-pending with a U.S. Plant Patent Application filed for a plant derived from the same breeding program that is entitled *Leucanthemum* Plant Named 'Shapcott Ruffles' (U.S. Plant patent application Ser. No. 13/815,086) and *Leucanthemum* Plant Named 'Shapcott Gossamer' (U.S. Plant patent application Ser. No. 13/815,088).

BACKGROUND OF THE INVENTION

The present invention relates to a new and distinct cultivar of *Leucanthemum×superbum* and will be referred to hereafter by its cultivar name, 'Shapcott Summer Clouds'. 'Shapcott Summer Clouds' represents a new Shasta daisy grown for landscape use and for use as a cut flower.

The new cultivar of *Leucanthemum* arose from an ongoing controlled breeding project by the Inventor in South Molton, Devon, United Kingdom. The new cultivar derived from crosses made in 1998 between unnamed proprietary plants in the Inventor's breeding program. Seeds were pooled from the crosses and the parents are unknown. The Inventor selected 'Shapcott Summer Clouds' as a single unique plant amongst the seedlings that resulted from the above crosses in 2001.

Asexual propagation of the new cultivar was first accomplished by division by the Inventor in 2001 in South Molton, Devon, United Kingdom. Asexual propagation by division has determined that the characteristics of this cultivar are stable and are reproduced true to type in successive generations.

SUMMARY OF THE INVENTION

The following traits have been repeatedly observed and represent the characteristics of the new cultivar. These attributes in combination distinguish 'Shapcott Summer Clouds' as a unique cultivar of *Leucanthemum.*

1. 'Shapcott Summer Clouds' exhibits capitulums with numerous fine ray florets (1 mm in width) that are arranged in a regular pattern nearly horizontal from the disk portion.
2. 'Shapcott Summer Clouds' reaches a height of 45 to 61 cm (18 to 24 inches).
3. 'Shapcott Summer Clouds' exhibits cold hardiness to −20° C.
4. 'Shapcott Summer Clouds' exhibits flower stems that stand erect and do not lodge.
5. 'Shapcott Summer Clouds' is dependably long-lived.
6. 'Shapcott Summer Clouds' exhibits deep green foliage.
7. 'Shapcott Summer Clouds' has been observed to be disease free under the conditions tested.
8. 'Shapcott Summer Clouds' exhibits flowers that are long lived as a cut flower.

The new *Leucanthemum* can be most closely compared to the cultivars 'H. Seibert' (not patented) and 'Horace Reid' (not patented). They are both similar to 'Shapcott Summer Clouds' in having capitulums with double ray florets. However, both differ from 'Shapcott Summer Clouds' in having ray florets that are less numerous and wider, in being a taller in height, and in having stems that tend to lodge without support. 'Shapcott Summer Clouds' can also be compared to the cultivars from the same breeding program; 'Shapcott Gossamer' and 'Shapcott Ruffles'. 'Shapcott Gossamer' differs from 'Shapcott Summer Clouds' in having capitulums with much less ray florets that are wider and longer and in being taller in height. 'Shapcott Ruffles' differs from 'Shapcott Summer Clouds' in having capitulums with ray florets that are less numerous, wider, and more irregular in aspect (reflexed, outward, and curled inward).

BRIEF DESCRIPTION OF THE DRAWINGS

The accompanying colored photographs illustrate the overall appearance and distinct characteristics of the new *Leucanthemum*. The photographs were taken of plants about 2 years in age as grown in a garden in South Molton, Devon, United Kingdom.

The photograph in FIG. 1 illustrates the plant habit of 'Shapcott Summer Clouds' in bloom.

Figure 1:
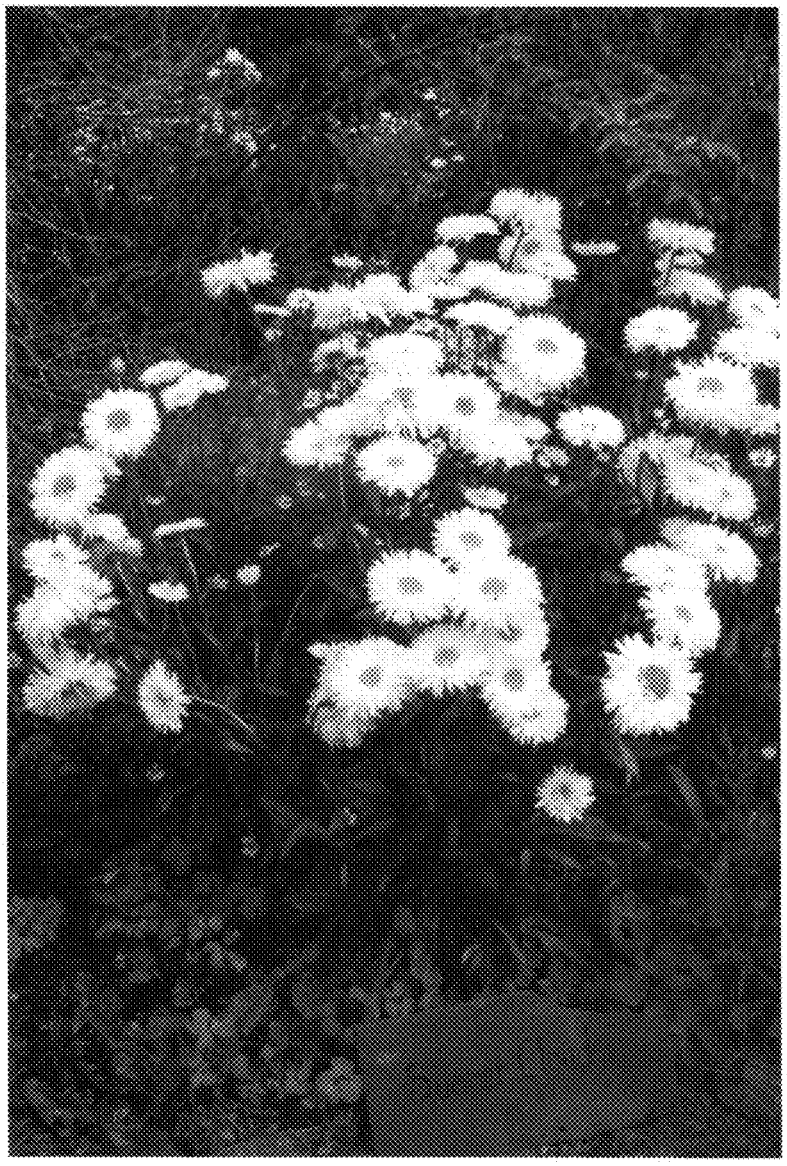
Figure 2:
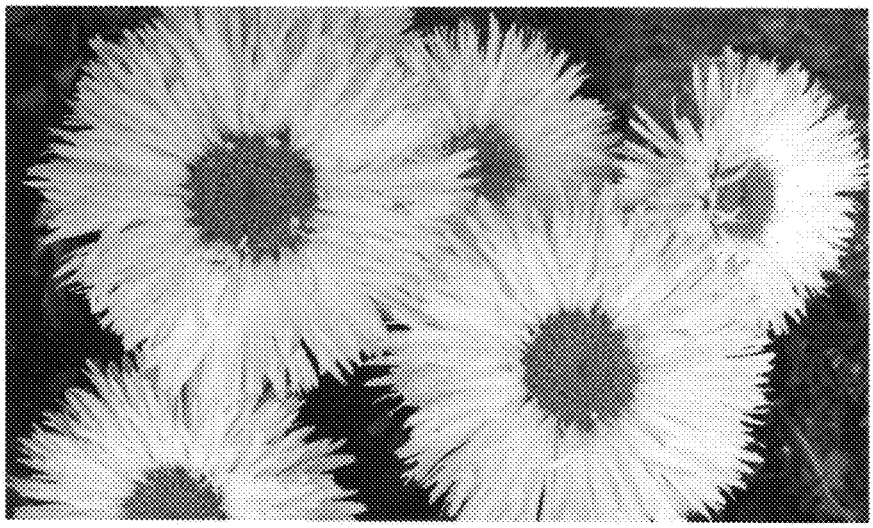

The photograph in FIG. 2 provides a close-up view of the capitulums of 'Shapcott Summer Clouds'.

Figure 3:
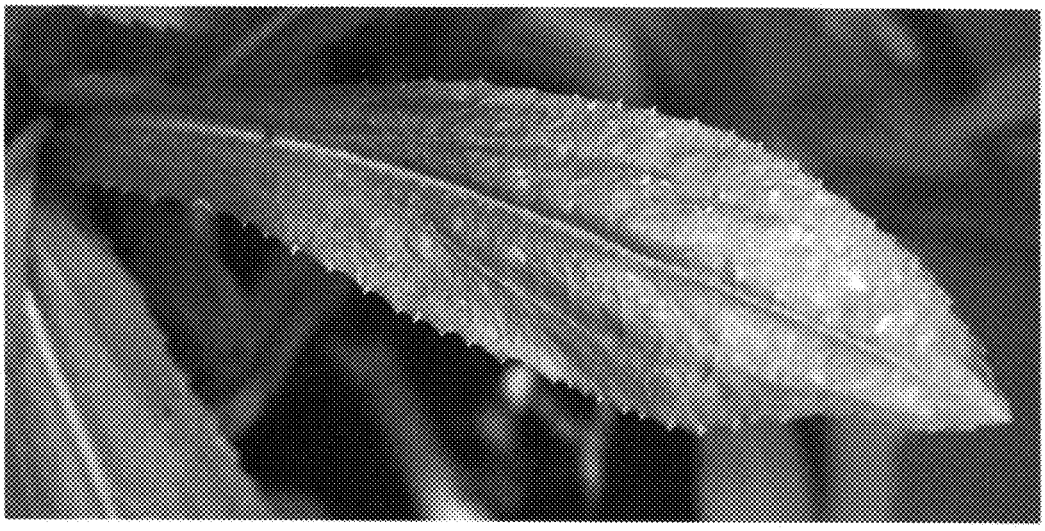

FIG. 3 provides a close-up view of a leaf of 'Shapcott Summer Clouds'.

The colors in the photographs may differ slightly from the color values cited in the detailed botanical description, which accurately describe the colors of the new *Leucanthemum*.

BOTANICAL DESCRIPTION OF THE PLANT

The following is a detailed description of three month-old plants from a division of the new cultivar as grown outdoors in 5.9-liter containers in Noordwijkerhout, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Blooms for 10 weeks from late June to early August in South Molton, Devon, United Kingdom.

*Plant type.*—Herbaceous perennial, long lived.

*Plant habit.*—Upright, freely branching.

*Height and spread.*—Reaches 45 to 61 cm (18 to 24 inches) in height and width.

*Diseases and pests.*—No susceptibility or resistance to diseases or pests has been observed.

*Cold hardiness.*—At least to −20° C.

*Environmental stresses.*—High wind tolerance, moderate rain tolerance and at least tolerant to +40° C.

*Root description.*—Fibrous roots, freely branched, dense.

*Growth rate.*—Moderately vigorous.

*Propagation.*—Division.

Stem description:

*Stem shape.*—Rounded.

*Stem aspect.*—Primarily upright without support.

*Stem strength.*—Very strong.

*Stem color.*—143B, axial ribs are 183A.

*Stem surface.*—Un-deep axial ribs, moderately glossy, sparsely covered in short strigose hairs average of 0.5 mm in length and 157D in color.

*Lateral branch size.*—Average of 49.5 cm in length and 8 mm in diameter.

*Quantity of lateral branches.*—About 3 per main branch.

*Internode length.*—Average of 2.2 cm.

*Branching.*—Moderately free branching.

Foliage description:

*Leaf division.*—Simple.

*Leaf shape.*—Oblanceolate.

*Leaf base.*—Cuneate, short decurrent.

*Leaf apex.*—Broadly acute.

*Leaf margin.*—Serrate.

*Leaf quantity.*—Average of 22 per lateral branch.

*Leaf venation.*—Pinnate, upper surface 143B to 143C in color, lower surface 144A in color and very sparse pubescence is along the main vein on the lower surface, average length of hairs is 0.5 mm and NN155D in color.

*Leaf attachment.*—Sessile.

*Leaf arrangement.*—Alternate.

*Leaf surface.*—Upper and lower surfaces; smooth and slightly glossy.

*Leaf color.*—Young foliage; upper surface between N137C and 143A, lower surface 143A, mature foliage; upper surface 137B, lower surface between 138A.

*Leaf size.*—Average of 12.8 cm in length and 2.7 cm in width.

Inflorescence description:

*Type.*—Capitulum, heterogamous with fine ligulate ray florets around disk florets in the center, borne on terminals and axillary nodes of lateral branches.

*Capitulum number.*—Average 10 ten per lateral stem, 30 per plant.

*Lastingness of inflorescence.*—About 3 weeks.

*Lastingness as a cut flower.*—About 7 days in water without additives.

*Capitulum size.*—Matures to about 4.2 cm in depth and 8 cm in diameter, disk size is about 2.5 cm in diameter, receptacle is 3 mm in height and 1.3 cm in diameter.

*Fragrance.*—None detected.

*Involucral bracts.*—About 50 arranged in 3 rows, about 9 mm in length and 3 mm in width, ovate in shape, broad acute apex, broad cuneate base, entire margin, smooth and dull on both surfaces, color; upper and lower surface; 143C, margins N199C.

*Buds.*—Flattened globular in shape, an average of 9 mm in length and 1.5 cm in diameter, 144C in color.

*Peduncle.*—Terminal peduncle; 21.5 cm in length and 2 mm in diameter, very strong, slightly glossy, smooth, with un-deep axial ribs, 143C in color and held straight upright, fourth peduncle; 26 cm in length and 2 mm in diameter very strong, slightly glossy, smooth, with un-deep axial ribs, 143C in color and held at an angle of 30°, seventh peduncle; 40 cm in length and 2 mm in diameter very strong, slightly glossy, smooth, with un-deep axial ribs, 143C in color and held at an angle of 30°.

*Ray florets* (*sterile*).—Rotate, Average of 100, arranged in multiple rows, cleft to parted in shape, held nearly horizontal, about 3.6 cm in length and 1 mm in width, cleft apex, attenuate base, entire margin, smooth on both surfaces, color: upper side; when opening and fully opened; NN155D, lower surface; when opening and fully opened; NN155D.

*Disk florets* (*bisexual*).—Numerous, about 250, rotate in shape, acute apex, lower 60% fused into a short tube, about 5 mm in length, 1 mm in width at base, 1.5 mm at apex, color: immature; 145A, base 151D, mature apex; 15C, mature mid-section; 145B, mature base; 151C to 151D.

Reproductive organs (present on disk florets only):

*Gynoecium.*—Pistil; 1, 2.5 mm in length, style; 2 mm in length and 151D in color, surrounded by stamens, stigma; decurrent in shape and 151D in color, ovary; 151D in color.

*Androcoecium.*—Stamens; 5, fused, form a cylinder around style, 3 mm in length, anther; basifixed and linear in shape, 2 mm in length and 151C in color, pollen; low and 13A in color.

*Fruit/seed.*—None observed.

It is claimed:

1. A new and distinct cultivar of *Leucanthemum* plant named 'Shapcott Summer Clouds' substantially as herein illustrated and described.

* * * * *